(12) United States Patent
Nabutovsky et al.

(10) Patent No.: US 8,385,999 B1
(45) Date of Patent: Feb. 26, 2013

(54) PROCESSING VENOUS OXYGEN SATURATION AND HEMATOCRIT INFORMATION IN AN IMPLANTABLE SENSOR

(75) Inventors: Yelena Nabutovsky, Mountain View, CA (US); Gene A. Bornzin, Simi Valley, CA (US); Taraneh Ghaffari Farazi, San Jose, CA (US); John W. Poore, South Pasadena, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1420 days.

(21) Appl. No.: 12/028,261

(22) Filed: Feb. 8, 2008

(51) Int. Cl.
*A61B 5/00* (2006.01)

(52) U.S. Cl. .......................................... 600/323; 607/22

(58) Field of Classification Search .................. 600/323, 600/508; 607/22
See application file for complete search history.

(56) References Cited

U.S. PATENT DOCUMENTS

| | | | |
|---|---|---|---|
| 4,776,340 A | 10/1988 | Moran et al. | |
| 4,813,421 A * | 3/1989 | Baudino et al. | 600/333 |
| 5,048,524 A * | 9/1991 | Bailey | 600/327 |
| 6,336,903 B1 | 1/2002 | Bardy | |
| 6,908,437 B2 | 6/2005 | Bardy | |
| 8,260,415 B2 * | 9/2012 | Donofrio | 607/6 |
| 2003/0092996 A1 | 5/2003 | Lowe et al. | |
| 2004/0123017 A1 | 6/2004 | Henry | |
| 2004/0147982 A1 | 7/2004 | Bardy | |
| 2005/0137481 A1 | 6/2005 | Sheard | |
| 2005/0234352 A1 | 10/2005 | Bardy | |
| 2007/0213622 A1 * | 9/2007 | Reisfeld | 600/484 |
| 2009/0163784 A1 * | 6/2009 | Sarpeshkar et al. | 600/322 |

FOREIGN PATENT DOCUMENTS

| | | |
|---|---|---|
| WO | 2005060652 A2 | 7/2005 |
| WO | 2005060652 A3 | 7/2005 |

OTHER PUBLICATIONS

Colin-Ramirez et al., "Body Composition and Echocardiographic Abnormalities Associated to Anemia and Volume Overload in Heart Failure Patients", Clin Nutr. May 12, 2006; (Epub ahead of print).

* cited by examiner

*Primary Examiner* — Max Hindenburg
*Assistant Examiner* — Renee Danega
(74) *Attorney, Agent, or Firm* — Steven M. Mitchell

(57) ABSTRACT

Methods of processing venous oxygen saturation and hematocrit information in an implantable sensor are provided. In an embodiment a method for collecting data from an implantable multi-wavelength SvO2 sensor having multiple light sources is provided. The method includes receiving a frame signal that indicates a beginning of the light sources being turned on and receiving a light source signal that indicates a light source is on. The output of a photodetector is sampled to measure the intensity of the transmitted light. The process is repeated for each light source to gather intensity measurements that then can be used to generate venous oxygen saturation and hematocrit measurements.

14 Claims, 6 Drawing Sheets

PROCESSING VENOUS OXYGEN SATURATION AND HEMATOCRIT INFORMATION IN AN IMPLANTABLE SENSOR

CROSS REFERENCE TO RELATED APPLICATIONS

The present invention is related to commonly owned U.S. Patent Application No. (to be assigned), entitled Assessing Medical Conditions Based on Venous Oxygen Saturation and Hematocrit Information, filed on even date herewith by Farazi et al., which is herein incorporated by reference in its entirety.

FIELD OF THE INVENTION

The present systems and methods relates to implantable medical devices, and more particularly, to processing oxygen saturation and hematocrit information measured by an implantable sensor.

BACKGROUND

Multi-wavelength intravenous optical sensors are used for measuring saturation of venous oxygen ("$SvO_2$") within humans and other animals. An example $SvO_2$ sensor projects two or more wavelengths of light into surrounding blood and measures the reflected light using a photodiode, separated from the light sources by an opaque barrier. The intensities of reflected light are combined into one or more ratios and oxygen saturation is extrapolated using an appropriate equation. Another type of $SvO_2$ sensor having an additional light source with the same wavelength as one of the light sources used for $SvO_2$ measurement allows for the sensor to also measure hematocrit.

Since the $SvO_2$ sensor resides in the bloodstream, the sensor is susceptible to the variations in the optical properties of the blood that may result from cardiac activity and respiration. Additionally, pulsatile blood flow, which accompanies regular contractions of the heart can have a strong effect on the signal.

What are needed are methods of accurately processing venous oxygen saturation and hematocrit information in an implantable sensor.

SUMMARY OF THE INVENTION

Methods of processing venous oxygen saturation and hematocrit information are disclosed. In an embodiment a method for collecting data from an implantable multi-wavelength SvO2 sensor having multiple light sources is provided. The method includes receiving a frame signal that indicates a beginning of the light sources being turned on and receiving a light source signal that indicates a light source is on. The output of a photodetector is sampled to measure the intensity of the transmitted light. The process is repeated for each light source to gather intensity measurements that then can be used to generate venous oxygen saturation and hematocrit measurements.

Further embodiments, features, and advantages of the systems and methods, as well as the structure and operation of the various embodiments of the system and methods are described in detail below with reference to accompanying drawings.

BRIEF DESCRIPTION OF THE FIGURES

The accompanying drawings, which are incorporated herein and form part of the specification, illustrate the methods and systems presented herein for processing venous oxygen saturation and hematocrit information in an implantable sensor. Together with the detailed description, the drawings further serve to explain the principles of and to enable a person skilled in the relevant art(s) to make and use the methods and systems presented herein.

In the drawings, like reference numbers indicate identical or functionally similar elements. Further, the drawing in which an element first appears is typically indicated by the leftmost digit(s) in the corresponding reference number (e.g., an element numbered 302 first appears in FIG. 3).

DETAILED DESCRIPTION OF THE INVENTION

The following detailed description of methods and systems for processing venous oxygen saturation and hematocrit information in an implantable sensor refers to the accompanying drawings that illustrate exemplary embodiments consistent with these methods and systems. Other embodiments are possible, and modifications may be made to the embodiments within the spirit and scope of the methods and systems presented herein. Therefore, the following detailed description is not meant to limit the methods and systems described herein. Rather, the scope of these methods and systems is defined by the appended claims.

It would be apparent to one of skill in the art that the methods and systems for processing venous oxygen saturation and hematocrit information in an implantable sensor as described below, may be implemented in many different embodiments of hardware, software, firmware, and/or the entities illustrated in the figures. Any actual software and/or hardware described herein is not limiting of these methods and systems. Thus, the operation and behavior of the methods and systems will be described with the understanding that modifications and variations of the embodiments are possible, given the level of detail presented herein.

Exemplary Environment

Overview

Before describing in detail the methods and systems for processing venous oxygen saturation and hematocrit information in an implantable sensor, it is helpful to describe an example environment in which these methods and systems may be implemented. The methods and systems described herein may be particularly useful in the environment of an implantable cardiac device (ICD) which is programmed via an external general purpose computer or via an external dedicated ICD programming device.

An ICD is a physiologic measuring device and therapeutic device that is implanted in a patient to monitor cardiac function and to deliver appropriate electrical therapy, for example, pacing pulses, cardioverting and defibrillator pulses, and drug therapy, as required. ICDs include, for example and without limitation, pacemakers, cardioverters, defibrillators, implantable cardioverter defibrillators, implantable cardiac rhythm management devices, and the like. Such devices may also be used in particular to monitor cardiac electrical activity and to analyze cardiac electrical activity. The term "implantable cardiac device" or simply "ICD" is used herein to refer to any such implantable cardiac device.

Figure 1:
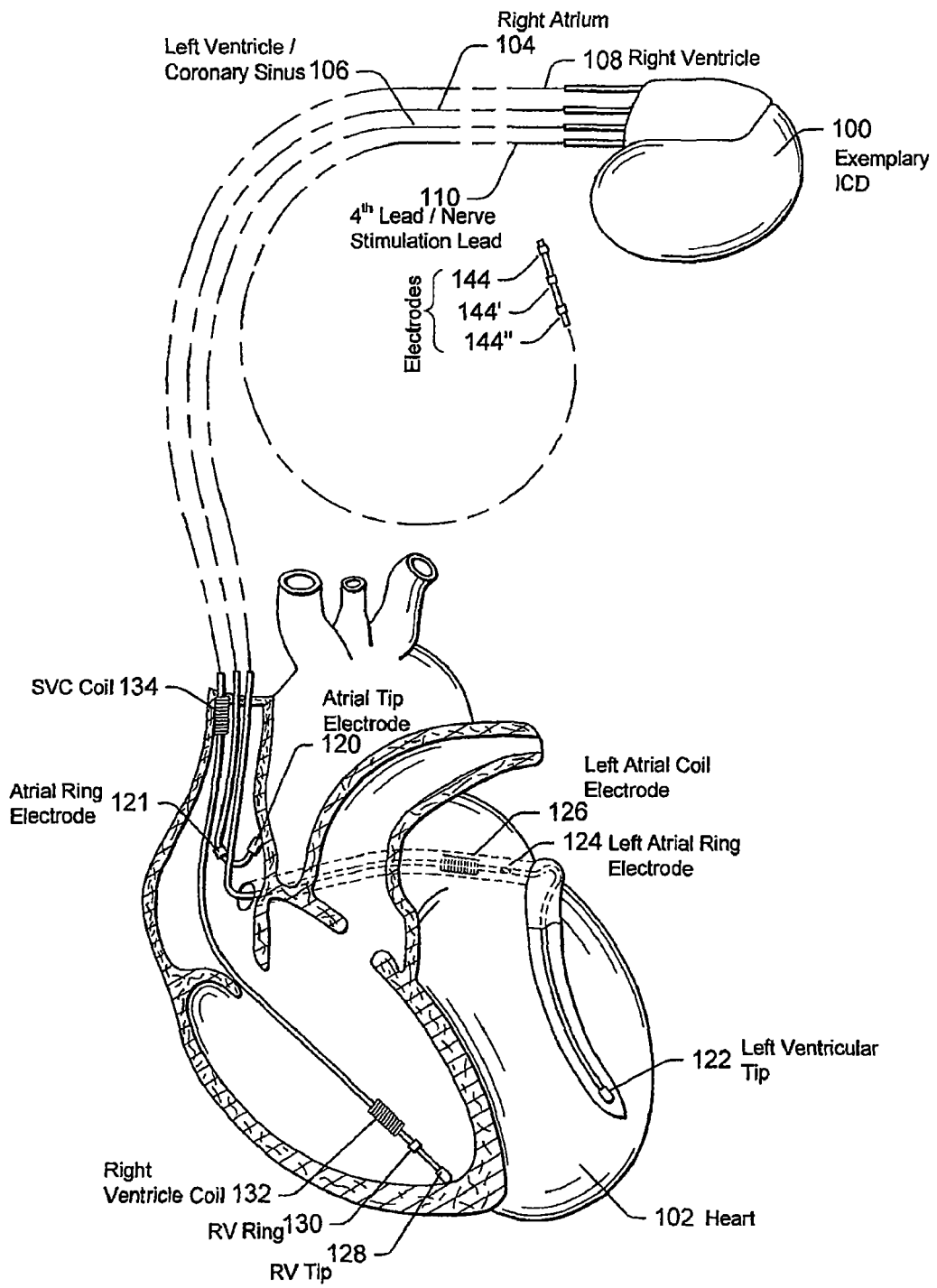
FIG. 1 is a simplified diagram illustrating an exemplary implantable cardiac device (ICD) in electrical communication with a patient's heart by means of leads suitable for delivering multi-chamber stimulation and pacing therapy, and for detecting cardiac electrical activity.
Figure 2:
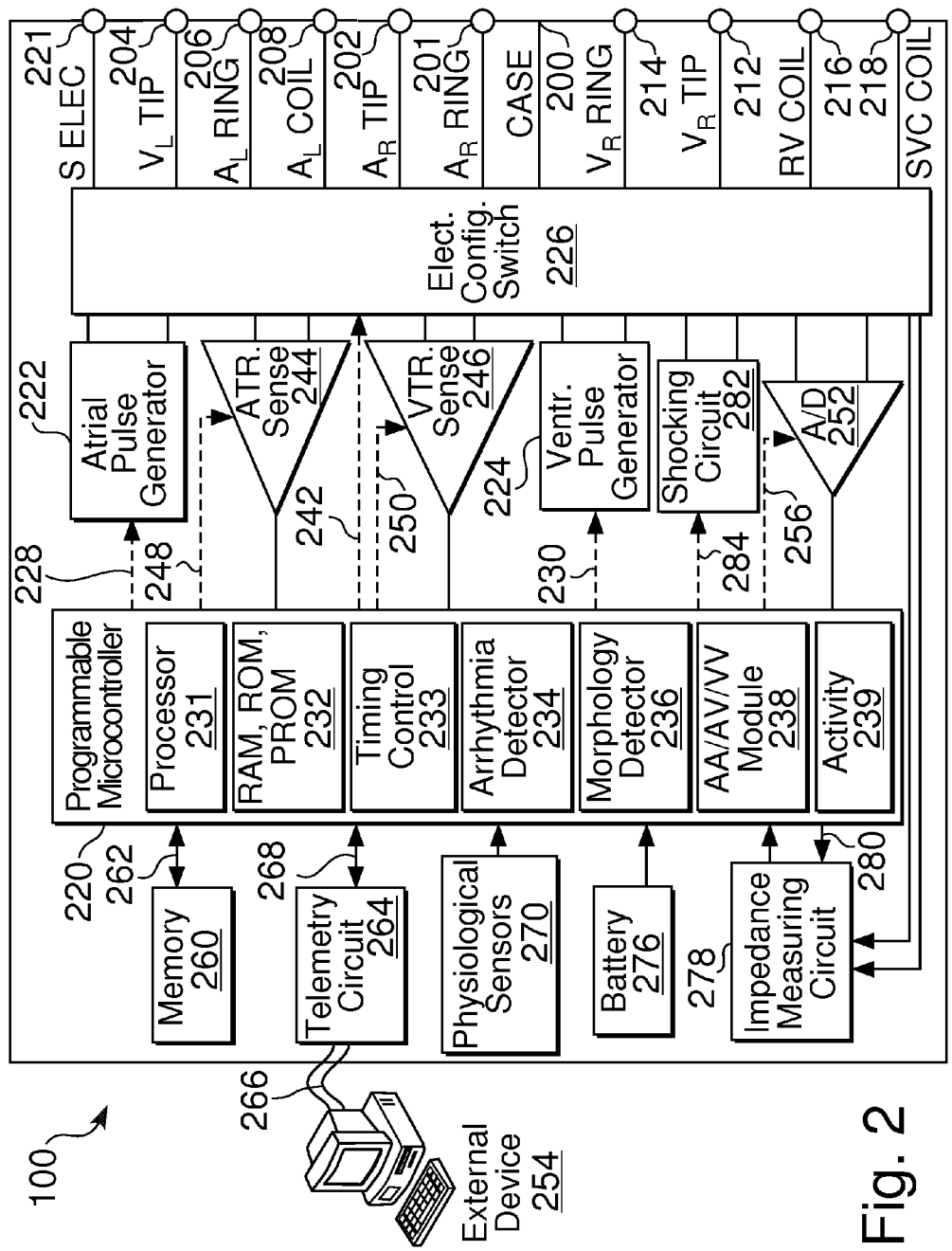
FIG. 2 is a functional block diagram of an exemplary ICD that can detect cardiac electrical activity and analyze cardiac electrical activity, as well as provide cardioversion, defibrillation, and pacing stimulation in four chambers of a heart.

FIGS. 1 and 2 illustrate such an environment.

Figure 3:
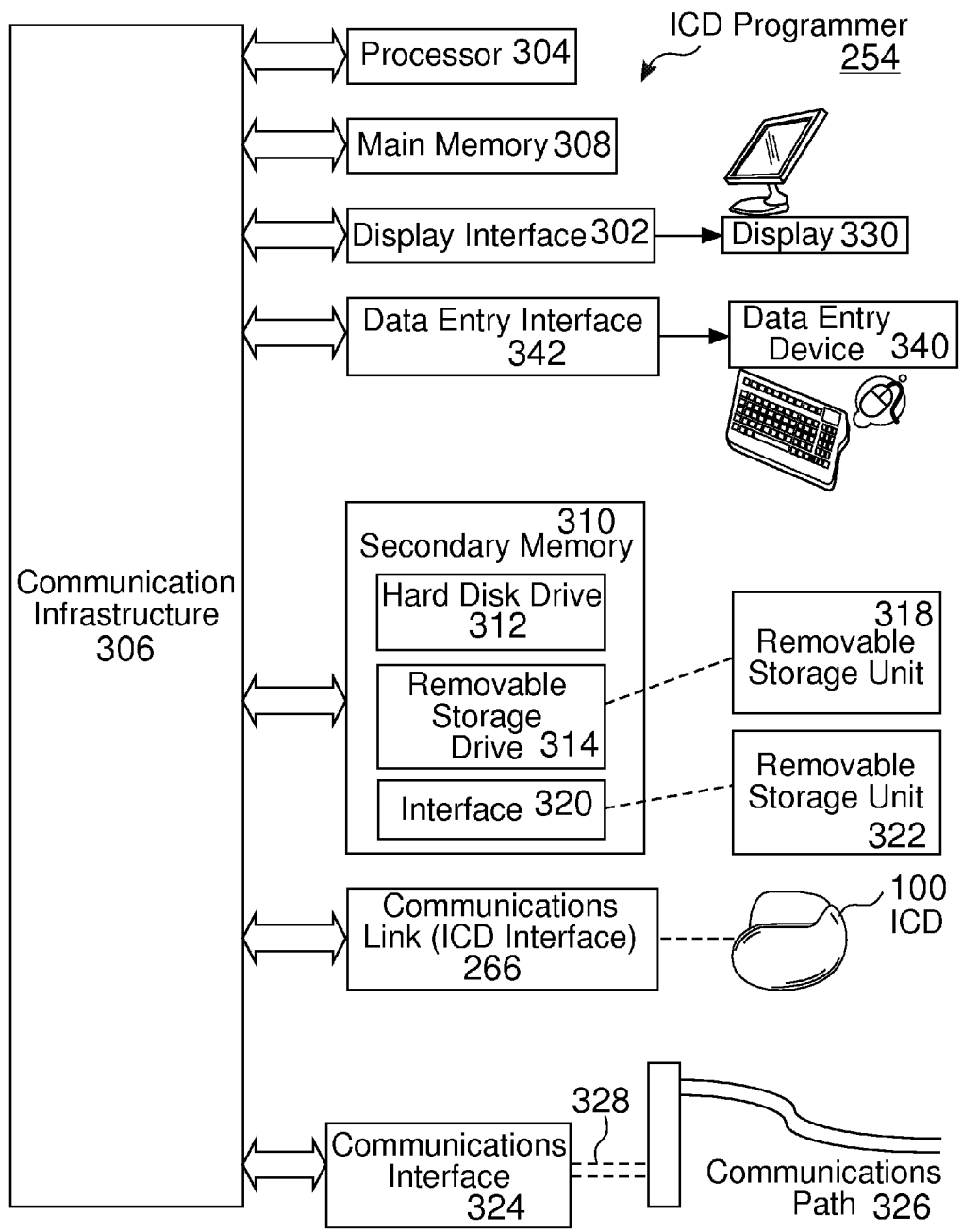
FIG. 3 is a functional block diagram of the internal architecture and principle external connections of an exemplary external programming device which may be used by a human programmer to monitor or program an ICD.

FIG. 3 illustrates the architecture of an external programming device which may be used by a human programmer to monitor, program, or interact with an ICD. While the architecture is described the context of an ICD, the architecture can be applied to other types of IMDs.

Exemplary ICD in Electrical Communication with a Patient's Heart

The techniques described below are intended to be implemented in connection with any ICD or any similar stimulation device that is configured or configurable to stimulate nerves and/or stimulate and/or shock a patient's heart.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead. In an embodiment, stimulation device 100, may also be coupled to or integrated with other sensors, such as a SvO2 sensor either directly or through communications with a programmer, such as ICD programmer 254, which is discussed below.

Functional Elements of an Exemplary ICD

An implantable cardiac device may be referred to variously, and equivalently, throughout this document as an "implantable cardiac device", an "ICD", an "implantable device", a "stimulation device", and the respective plurals thereof.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 (see FIG. 1) for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, shocking, and/or autonomic stimulation, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a processor or microprocessor 231, or equivalent control circuitry, designed specifically for controlling the delivery of stimulation therapy, and may further include onboard memory 232 (which may be, for example and without limitation, RAM, ROM, PROM, one or more internal registers, etc.), logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 233 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module (the latter two are not shown in FIG. 2). These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. Such a module may help make determinations as to fusion.

The microcontroller 220 of FIG. 2 also includes an activity module 239. This module may include control logic for one or more activity related features. For example, the module 239 may include an algorithm for determining patient activity level, calling for an activity test, calling for a change in one or more pacing parameters, etc. These algorithms are described in more detail with respect to the figures. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

When coupled with or integrated to another type of sensor, such as an SvO$_2$ sensor, Microcontroller 220 may also include a sensor control module that is coupled to the sensor. The sensor control module integrates the operation of simulation device 100 with the one or more coupled sensors.

The electrode configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the analog-to-digital (A/D) data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (ND) data acquisition system 252. The data acquisition system 252 is configured to acquire intracardiac electrogram (EGM) signals, convert the raw analog data into a digital signal, and store the digital signals for later processing and/or telemetric transmission to an external device 254. Data acquisition system 252 may be configured by microcontroller 220 via control signals 256. The data acquisition system 252 is coupled to the right atrial lead 104, the coronary sinus lead 106, the right ventricular lead 108 and/or the nerve stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature may be the ability to sense and store a relatively large amount of data (e.g., from the data acquisition system 252), which data may then be used for subsequent analysis to guide the programming of the device.

Essentially, the operation of the ICD control circuitry, including but not limited to pulse generators, timing control circuitry, delay modules, the activity module, and sensing and detection circuits, may be controlled, partly controlled, or fine-tuned by a variety of parameters, such as those indicated above which may be stored and modified, and may be set via an external ICD programming device.

Advantageously, the operating parameters of the implantable device 100 may be non-invasively programmed into the memory 260 through a telemetry circuit 264 in telemetric communication via communication link 266 with the external device 254, such as a general purpose computer, a dedicated ICD programmer, a transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266. The ICD 100 may also receive human programmer instructions via the external device 254.

In other embodiments, ICD Programmer 254 may include interfaces to other IMD devices. These interfaces can then be used to collect, for example, hematocrit and $SvO_2$ measurements for $SvO_2$ sensors, for example. ICD Programmer 254 uses these interfaces to collect measurements that then can be used with the methods described below for processing venous oxygen saturation and hematocrit information in an implantable sensor.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 may respond by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of an example activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 □A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuit 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

ICD Programmer

As indicated above, the operating parameters of the implantable device 100 may be non-invasively programmed into the memory 260 through a telemetry circuit 264 in telemetric communication via communication link 266 with the external device 254. The external device 254 may be a general purpose computer running custom software for programming the ICD 100, a dedicated external programmer device of ICD 100, a transtelephonic transceiver, or a diagnostic system analyzer. Generically, all such devices may be understood as embodying computers, computational devices, or computational systems with supporting hardware or software which enable interaction with, data reception from, and programming of ICD 100.

Throughout this document, where a person is intended to program or monitor ICD 100 (where such person is typically a physician or other medical professional or clinician), the person is always referred to as a "human programmer" or as a "user". The term "human programmer" may be viewed as synonymous with "a person who is a user of an ICD programming device", or simply with a "user". Any other reference to "programmer" or similar terms, such as "ICD programmer", "external programmer", "programming device", etc., refers specifically to the hardware, firmware, software, and/or physical communications links used to interface with and program ICD 100.

The terms "computer program", "computer code", and "computer control logic" are generally used synonymously and interchangeably in this document to refer to the instructions or code which control the behavior of a computational system. The term "software" may be employed as well, it being understood however that the associated code may in some embodiments be implemented via firmware or hardware, rather than as software in the strict sense of the term (e.g., as computer code stored on a removable medium, or transferred via a network connection, etc.).

A "computer program product" or "computational system program product" is a medium (for example, a magnetic disk drive, magnetic tape, optical disk (e.g., CD, DVD), firmware, ROM, PROM, flash memory, a network connection to a server from which software may be downloaded, etc) which is suitable for use in a computer or computation system, or suitable for input into a computer or computational system, where the medium has control logic stored therein for causing a processor of the computational system to execute computer code or a computer program. Such medium, also referred to as "computer program medium", "computer usable medium", and "computational system usable medium", are discussed further below.

FIG. 3 presents a system diagram representing an exemplary computer, computational system, or other programming device, which will be referred to for convenience as ICD programmer 254. It will be understood that while the device is referred to an "ICD programmer", indicating that the device may send programming data, programming instructions, programming code, and/or programming parameters to ICD 100, the ICD programmer 254 may receive data from ICD 100 as well, and may display the received data in a variety of formats, analyze the received data, store the received data in a variety of formats, transmit the received data to other computer systems or technologies, and perform other tasks related to operational and/or physiologic data received from ICD 100.

Various embodiments of the present system and method are described in terms of this exemplary ICD programmer 254. After reading this description, however, it will become apparent to a person skilled in the relevant art(s) how to implement the system and method using other computer systems and/or architectures.

ICD programmer 254 includes one or more processors, such as processor 304. Processor 304 is used for standard computational tasks well known in the art, such as retrieving instructions from a memory, processing the instructions, receiving data from memory, performing calculations and analyses on the data in accordance with the previously indicated instructions, storing the results of calculations back to memory, programming other internal devices within ICD programmer 254, and transmitting data to and receiving data from various external devices such as ICD 100.

Processor 304 is connected to a communication infrastructure 306 which is typically an internal communications bus of ICD programmer 254; however, if ICD programmer 254 is implemented in whole or in part as a distributed system, communication infrastructure 306 may further include or may be a network connection.

ICD programmer 254 may include a display interface 302 that forwards graphics, text, and other data from the communication infrastructure 306 (or from a frame buffer not shown) for display on a display unit 330. The display unit may be, for example, a CRT, an LCD, or some other display device. Display unit 330 may also be more generally understood as any device which may convey data to a human programmer.

Display unit 330 may also be used to present a user interface which displays internal features of, operating modes or parameters of, or data from ICD 100. The user interface presented via display unit 330 of ICD programmer 254 may include various options that may be selected, deselected, or otherwise changed or modified by a human programmer of ICD 100. The options for programming the ICD 100 may be presented to the human programmer via the user interface in the form of buttons, check boxes, menu options, dialog boxes, text entry fields, or other icons or means of visual display well known in the art.

ICD programmer 254 may include a data entry interface 342 that accepts data entry from a human programmer via data entry devices 340. Such data entry devices 340 may include, for example and without limitation, a keyboard, a mouse, a touchpad, a touch-sensitive screen, a microphone for voice input, or other means of data entry, which the human programmer uses in conjunction with display unit 330 in a manner well known in the art. For example, either a mouse or keystrokes entered on a keyboard may be used to select check boxes, option buttons, menu items, or other display elements indicating human programmer choices for programming ICD 100. Direct text entry may be employed as well. Data entry device 340 may also take other forms, such as a dedicated control panel with specialized buttons and/or other mechanical elements or tactile sensitive elements for programming ICD 100.

In the context of the present system and method, display interface 302 may present on display unit 330 a variety of data related to patient cardiac function and performance, and also data related to the current operating mode, operational state, or operating parameters of ICD 100. Modifications to ICD 100 operational state(s) may be accepted via data entry interface 342 and data entry device 340. In general, any interface means which enables a human programmer to interact with and program ICD 100 may be employed. In one embodiment, for example, a visual data display may be combined with tactile data entry via a touch-screen display.

In another embodiment, a system of auditory output (such as a speaker or headset and suitable output port for same, not shown) may be employed to output data relayed from ICD 100, and a system of verbal input (such as a microphone and suitable microphone port, not shown) may be employed to program ICD 100. Other modes of input and output means may be employed as well including, for example and without limitation, a remote interaction with ICD 100, viewing printed data which has been downloaded from ICD 100, or the programming of ICD 100 via a previously coded program script.

All such means of receiving data from ICD 100 and/or programming ICD 100 constitute an interface 302, 330, 342, 340 between ICD 100 and a human programmer of ICD 100, where the interface is enabled via both the input/output hardware (e.g., display screen, mouse, keyboard, touchscreen, speakers, microphone, input/output ports, etc.) and the hardware, firmware, and/or software of ICD programmer 254.

ICD programmer 254 also includes a main memory 308, preferably random access memory (RAM), and may also include a secondary memory 310. The secondary memory 310 may include, for example, a hard disk drive 312 and/or a removable storage drive 314, representing a floppy disk drive, a magnetic tape drive, an optical disk drive, etc. The removable storage drive 314 reads from and/or writes to a removable storage unit 318 in a well known manner. Removable storage unit 318 represents a magnetic disk, magnetic tape, optical disk, etc. which is read by and written to by removable storage drive 314. As will be appreciated, the removable storage unit 318 includes a computer usable storage medium having stored therein computer software and/or data.

In alternative embodiments, secondary memory 310 may include other similar devices for allowing computer programs or other instructions to be loaded into ICD programmer 254. Such devices may include, for example, a removable storage unit 322 and an interface 320. Examples of such may include a program cartridge and cartridge interface (such as that found in video game devices), a removable memory chip (such as an erasable programmable read only memory (EPROM), programmable read only memory (PROM), or flash memory) and associated socket, and other removable storage units 322 and interfaces 320, which allow software and data to be transferred from the removable storage unit 322 to ICD programmer 254.

ICD programmer 254 also contains a communications link 266 to ICD 100, which may be comprised in part of a dedicated port of ICD programmer 254. From the perspective of ICD programmer 254, communications link 266 may also be viewed as an ICD interface. Communications link 266 enables two-way communications of data between ICD programmer 254 and ICD 100. Communications link 266 has been discussed above (see the discussion of FIG. 2).

ICD programmer 254 may also include a communications interface 324. Communications interface 324 allows software and data to be transferred between ICD programmer 254 and other external devices (apart from ICD 100). Examples of communications interface 324 may include a modem, a network interface (such as an Ethernet card), a communications port, a Personal Computer Memory Card International Association (PCMCIA) slot and card, etc. Software and data transferred via communications interface 324 are in the form of signals 328 which may be electronic, electromagnetic, optical or other signals capable of being received by communications interface 324. These signals 328 are provided to communications interface 324 via a communications path (e.g., channel) 326. This channel 326 carries signals 328 and may be implemented using wire or cable, fiber optics, a telephone line, a cellular link, an radio frequency (RF) link and other communications channels.

The terms "computer program medium", "computer usable medium", and "computational system usable medium" are used, synonymously, to generally refer to media such as removable storage drive 314, a hard disk installed in hard disk drive 312, and signals 328. These computer program products or computational system program products provide software to ICD programmer 254.

It should be noted, however, that it is not necessarily the case that the necessary software, computer code, or computer program (any of which may also referred to as computer control logic) be loaded into ICD programmer 254 via a removable storage medium. Such computer program may be loaded into ICD programmer 254 via communications link 328, or may be stored in memory 308 of ICD programmer 254. Computer programs are stored in main memory 308 and/or secondary memory 310. Computer programs may also be received via communications interface 324. Such computer programs, when executed, enable the ICD programmer 254 to perform the features of the present system and method, as discussed herein. In particular, the computer programs, when executed, enable the processor 304 to perform the features of the present system and method. Accordingly, such computer programs represent controllers of ICD programmer 254, and thereby controllers of ICD 100.

In an embodiment where the present system and method is implemented using software, the software may be stored in a computer program product and loaded into ICD programmer 254 using removable storage drive 314, hard drive 312 or communications interface 324. The control logic (software), when executed by the processor 304, causes the processor 304 to perform the functions of the system and method as described herein. Alternatively when the present system and method is implemented using software, the software may be preloaded or loaded via a programmer, such as ICD programmer 254, onto an IMD, such as ICD 100 or an implantable SvO2 sensor, for example.

SvO$_2$ Sensor Data Collection

Figure 4:
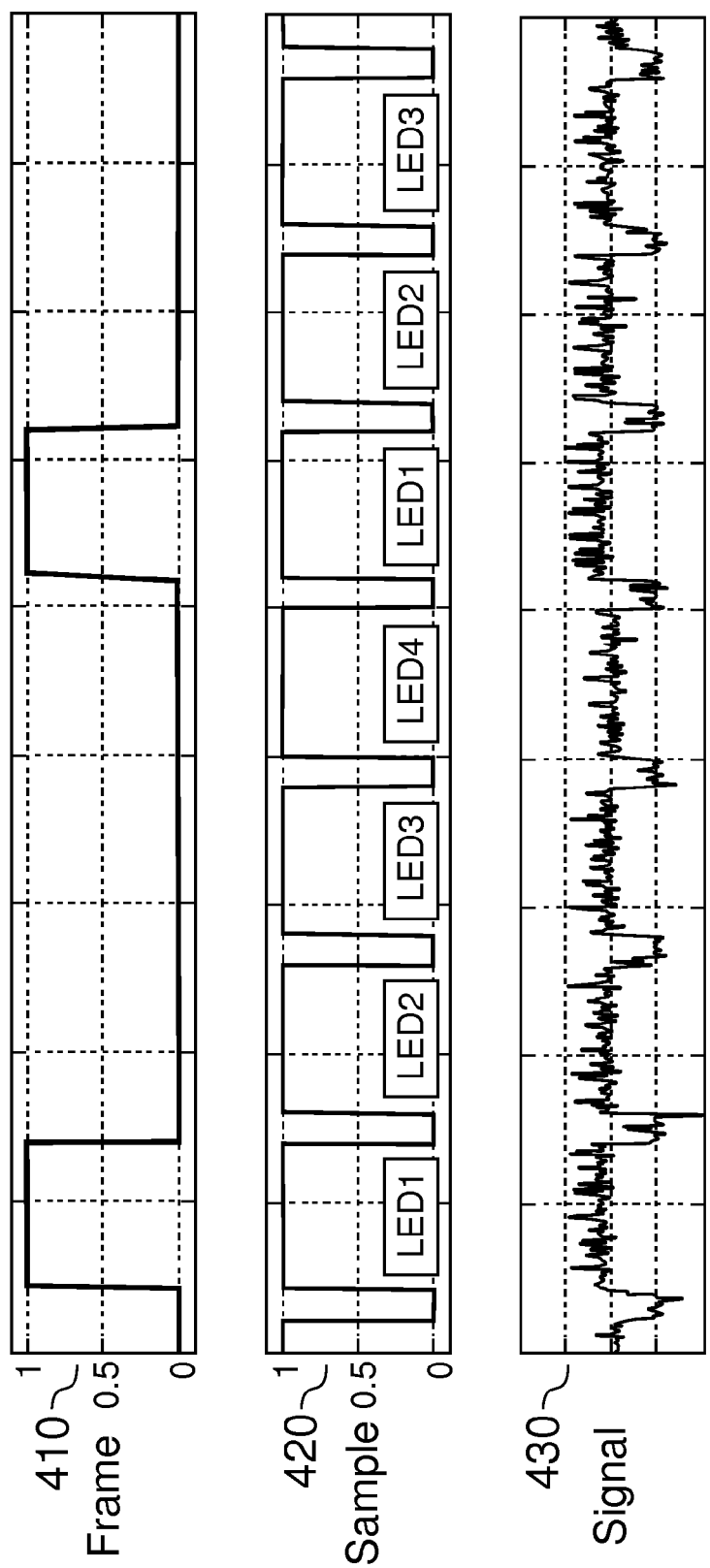
FIG. 4 provides a series of signals including a frame signal, a sample signal and an $SvO_2$ data signal.

FIG. 4 illustrates frame signal 410 and sample signal 420 used to sample SvO$_2$ data signal 430. In a multiple wavelength SvO$_2$ sensor containing multiple light sources, e.g., light emitting diodes sources ("LEDs"), the light sources are turned ON in a series. The sensor signal should be sampled only when the corresponding light source is turned ON. As indicated in FIG. 4, frame signal 410 and sample signal 420 can be used to indicate when which light source is on. Frame signal 410 indicates the beginning of cycling on each LED within the set of LEDs in an SvO$_2$ sensor. FIG. 4 indicates that the sensor includes four LEDs within the series. The present systems and methods are not limited to a sensor having four LEDs, but apply to any sensor having multiple wavelength light transmissions. Sample signal 420 indicates when to sample the signal from each LED. Data signal 430 represents the received SvO$_2$ data signal based on the detection of the light emitted by the LED at a photodetector.

Figure 5:
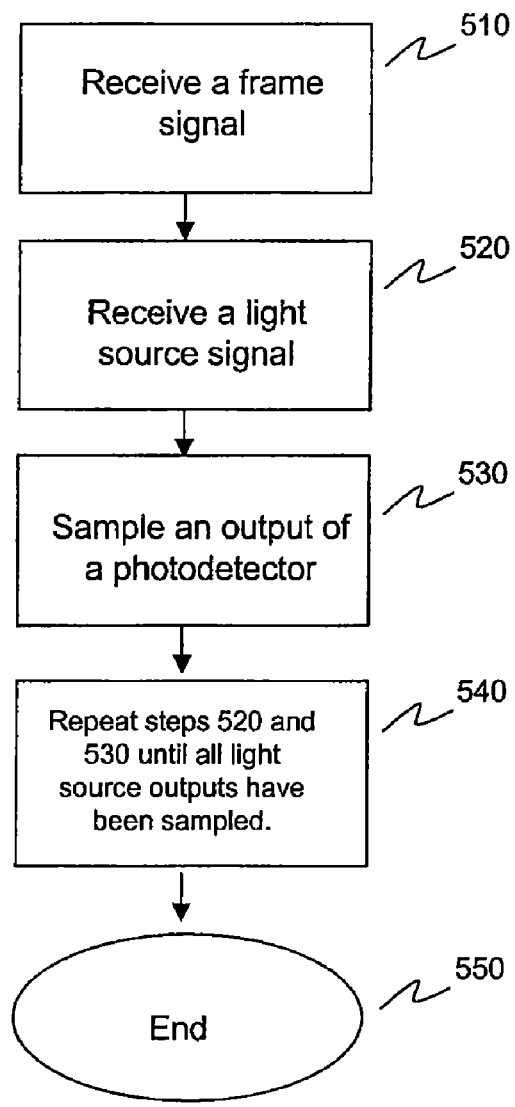
FIG. 5 is a flow chart of a method for collecting data from an implantable multi-wavelength $SvO_2$ sensor having multiple light sources.

FIG. 5 provides a flowchart of method 500 for collecting data from an implantable multi-wavelength SvO$_2$ sensor having multiple light sources. Method 500 begins in step 510.

In step 510, a frame signal that indicates a beginning of the light sources being turned ON is received. For example, a microprocessor within a sensor for processing data signal 430 can receive frame signal 410 from another processor within the sensor, or from an external source.

In step 520, a light source signal that indicates a light source is on is received. For example, a microprocessor within a sensor for processing data signal 430 can receive a sample signal 420 from another processor within the sensor, or from an external source.

In step 530, an output of a photodetector associated with the light source that is on is sampled. In an embodiment, the sensor waits a predefined or programmable amount of time prior to sampling the photodetector output. The sensor also records samples for a predetermined amount of time or for a predetermined number of samples. Alternatively, instead of sampling a certain number of data points, the sensor can record the samples until the end of the sample signal 420 for a particular light source. The data collected while each sample signal 420 is on can either be combined into a single point by averaging, taking a median or performing a similar mathematical operation, or complete data can be stored until data from light sources with all the wavelengths has been collected.

Alternatively, a separate sample signal 420 may not be needed if a microprocessor in the sensor that turns the light sources on also performs the sampling. In this case, when the microprocessor turns on the corresponding light source, the microprocessor can also begin the sampling either right away or following a predefined/programmable period of time. The microprocessor can either sample a predefined/programmable number of points or simply stop sampling when the microprocessor turns off the light source.

In an alternative embodiment, one of the sample signals 420 can be used to replace the frame signal 410. Instead of having a separate frame signal 410, the first sample signal 420 in each set of four (or however many LEDs are within the sensor) could have a different characteristic to indicate that it is the first in the set of sample signals. For example, the first sample signal 410 could be shorter than the other sample signals.

In step 540, steps 520 through 530 are repeated until outputs from each light source have been sampled. That is, each of the light sources is turned ON in series, and measurements are taken corresponding to each light source. In step 550, method 500 ends.

After each frame of data has been collected, the data can be combined into ratios for the $O_2$ saturation and hematocrit calculations. The hematocrit (Ht or HCT) is a measure of the proportion of blood volume that is occupied by red blood cells. This can be performed either after each frame of data, or to reduce noise, data can be accumulated for a preset or programmable amount of time. In this scenario, once a set of data is collected, the data is filtered, averaged and then combined into ratios for the $O_2$ saturation and hematocrit calculations. An example of a filter is a median filter. Alternatively, the ratios, $O_2$ saturation and hematocrit can be found continuously after each frame for a period of data and then filtered and averaged to output final values.

Figure 6:
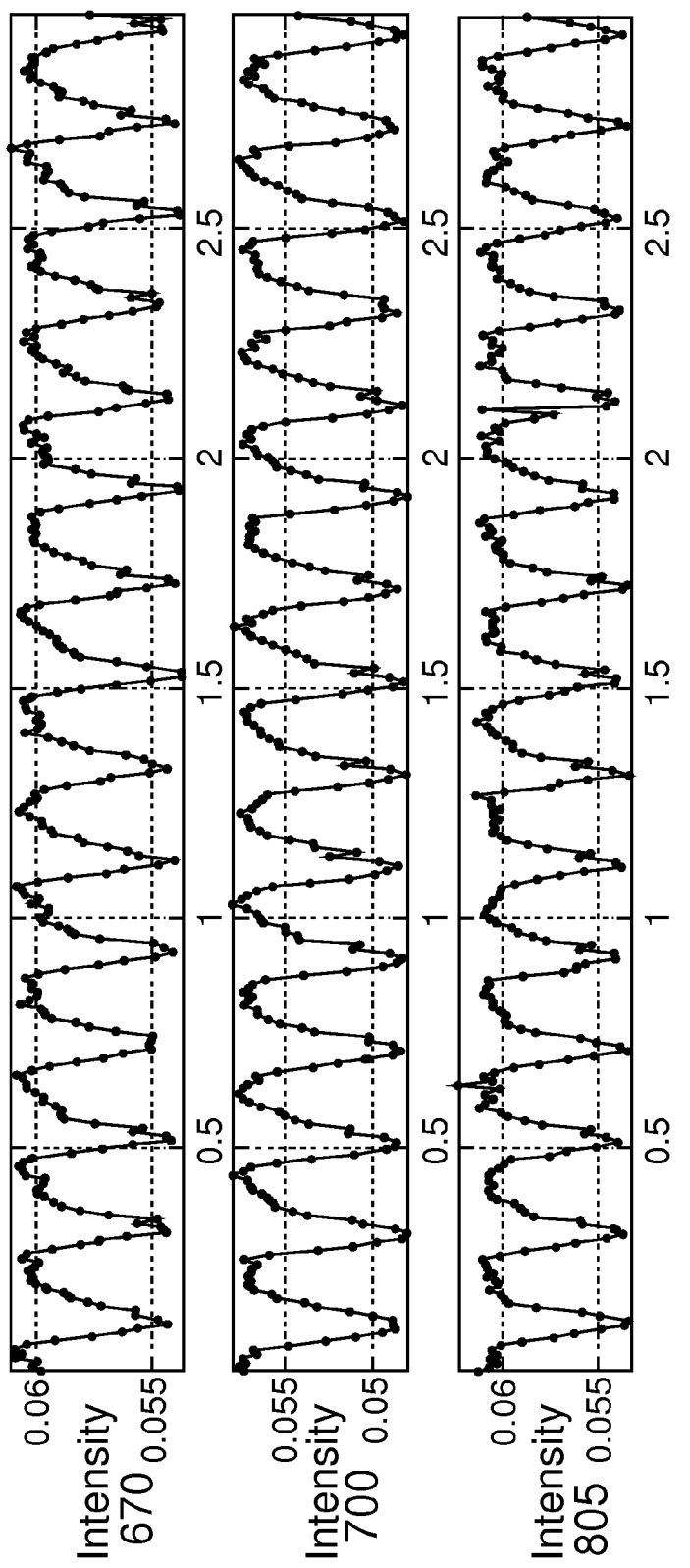
FIG. 6 illustrates an example $SvO_2$ signal in the presence of strong pulsatile action of the vessels.

During each period of data collection, data can be collected continuously, periodically or based on a trigger. The trigger can include, but is not limited to, a trigger from another sensor; an R-wave or P-wave detector from subcutaneous, epicardial or endocardial electrograms ("EGMs"), a pacing pulse; or a self-generated trigger signal. In the latter case, in an embodiment the trigger signal can be generated by analyzing the pulsatile component of a strong pulsatile action of the blood vessels. FIG. 6 illustrates an example $SvO_2$ signal in the presence of strong pulsatile action of the vessels. Within FIG. 6, three graphs are provided that show the light intensity measured from a 670 nm, 700 nm and 805 nm LED within an $SvO_2$ sensor. In each case, the signal is smoothed with each point corresponding to an average of 10 ms of data. The periodic intensity readings demonstrate a strong pulsatile component in each of the traces.

To ensure consistency in the data measurements, in an embodiment only a portion of the pulse is used for sampling measurement data. For example, only the peaks of the pulses can be used for sampling measurement data. Each peak could include either just the local maximum or the local maximum and several points on either side averaged or otherwise combined together. Similarly, in another embodiment, only the troughs can be used for sampling measurement data.

In another embodiment, a certain predefined/programmable time window can determine when the sensor data is taken. There may also be a delay or blanking period defined following the trigger signal. These two timing parameters ensure that data is collected during the same condition each time (e.g., end diastole versus end systole). If respiration information is available, it can also be incorporated into the calculation to determine an appropriate sampling window. The $SvO_2$ value generated by the sensor algorithm may be, but is not limited to an average, maximum, median or combination thereof, representative value of the measurements over M cardiac cycles, all cardiac cycles in N respiration cycles, or the first P cardiac cycles in Q consecutive respiration cycles.

In the course of the hour, day, week or other time period, data can be collected continuously at all times or periodically with a predefined or programmable time period. As described above, there can be a trigger signal to define the start of measurement. The trigger signal may be from another sensor or self-generated. The data collection can continue for a predefined period or end on a trigger. The data may also be collected sparingly, at a long time interval. However, in an embodiment, if the sensor detects that the $O_2$ saturation drops below a predefined or programmable threshold, the data will be collected at a different time interval (e.g., more often). The different time intervals can be predefined or programmable as a function of $O_2$ saturation.

CONCLUSION

Exemplary embodiments of the present systems and methods have been presented. The systems and methods are not limited to these examples. These examples are presented herein for purposes of illustration, and not limitation. Alternatives (including equivalents, extensions, variations, deviations, etc., of those described herein) will be apparent to persons skilled in the relevant art(s) based on the teachings contained herein. Such alternatives fall within the scope and spirit of the systems and methods herein.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present system and method in any way.

What is claimed is:

1. A method for collecting data from an implantable multi-wavelength venous oxygen ($SvO_2$) sensor having multiple light sources, comprising:
   (a) receiving a first signal in response to a peak of a pulsatile action of a blood vessel;
   (b) turning on a light source of the multiple light sources in response to the first signal;
   (c) receiving a second signal that indicates the light source is on;
   (d) sampling, in response to the second signal, an output of a photodetector to measure the intensity of the light source that is on, such that the sampling occurs during the peak of the pulsatile action; and
   (e) repeating steps (b) through (d) until outputs corresponding to each of the multiple light sources have been sampled.

2. The method of claim 1, wherein the second signal is a light source signal.

3. The method of claim 1, wherein the first signal and the second signal are the same signal.

4. The method of claim 1, farther comprising turning on each of the multiple light sources in a series.

5. The method of claim 1, further comprising inserting a blanking interval prior to the sampling, wherein the blanking interval ensures that data is collected during the same condition each time data is sampled.

6. The method of claim 1, further comprising delaying sampling an output of a photodetector associated with the light source that is on for a predetermined time interval following receiving the second signal that indicates the light source is on.

7. The method of claim 1, wherein sampling an output of a photodetector associated with the light source includes sampling a predefined number of sample points.

8. The method of claim 1, wherein sampling an output of a photodetector associated with the light source includes taking samples from the photodetector until the second signal indicates that the light source is off.

9. The method of claim 1, wherein a sampling interval for sampling an output of a photodetector varies as a function of respiration information.

10. The method of claim 1, further comprising combining data collected during sampling from each light source into a single data point by averaging the collected data or by generating a median of the collected data.

11. The method of claim 1, further comprising storing data collected during sampling from each light source until data based on all light sources has been collected.

12. The method of claim 1, further comprising combining the data received from each of the light sources into ratios for $O_2$ saturation and hematocrit calculations.

13. The method of claim 12, further comprising:
   (i) accumulating data received from each of the light sources for a predetermined period of time; and
   (ii) filtering data received from each of the light sources.

14. The method of claim 13, wherein filtering data received from each of the light sources includes applying a median filter to the received data for each light source.

* * * * *